United States Patent [19]

Stern

[11] Patent Number: 5,831,022
[45] Date of Patent: Nov. 3, 1998

[54] PURIFICATION OF RECOMBINANT HUMAN IL-1α

[75] Inventor: Alvin Seth Stern, Passaic Park, N.J.

[73] Assignee: Hoffmann-La Roche Inc., Nutley, N.J.

[21] Appl. No.: 830,406

[22] Filed: Feb. 18, 1986

[51] Int. Cl.⁶ .......................... C07K 14/52; A61K 38/20
[52] U.S. Cl. .................... 530/351; 530/412; 530/413; 530/416; 530/417; 530/418; 530/419; 530/420; 930/141; 424/85.2; 435/69.52
[58] Field of Search ..................... 530/351, 412, 530/416, 417, 825; 435/68, 70

[56] References Cited

U.S. PATENT DOCUMENTS

| 4,675,387 | 6/1987 | Korant .......................................... 424/85 |

FOREIGN PATENT DOCUMENTS

| 0114506 | 8/1984 | European Pat. Off. . | |
| 3432196 | 3/1986 | Germany ................................. | 435/68 |
| 0149386 | 8/1985 | Japan . | |
| 8500830 | 2/1985 | WIPO . | |

OTHER PUBLICATIONS

Mizel et al, *J Immunol* 126(3) 1981, pp. 834–837.
Cameron et al, J Exp Med, 162, 1985, pp. 790–801.
Cameron et al, J Exp Med 164, 1986 pp. 237–250.
Matsushima et al, Fourth International Lymphokine Workshop: Molecular & Cellular Biology of Lymphokines Oct. 1984 *Lymphokine Res.*
Matsushima et al, Cell Immunol 92, 1985 pp. 290–301.
Kronheim et al, *J Exp Med* 161, 1985 pp. 495–502.
Lachman et al, *J Supramolecular Structure* vol. 13(4) 1980, pp. 457–466.
Schmidt, *J Exp Med* 160, 1984, pp. 772–787.
Lomedico, *Nature* 312, 1984, pp. 457–462.
Mizel et al, *J Immunol*, vol. 126, 1981 pp. 834–837.
Gray et al *J Immunol* vol. 137, 1986, pp. 3644–3648.
Windle et al J Immunol 132(5) 1984, pp. 1317–1323.
Furutani et al *N.A. Res* 14(8) 1986, pp. 3167–3178.
Clark et al *N.A. Res* 14(20) 1986 pp. 7897–7914.
Krakauer et al CA vol. 102, 1985, #219322g.
Prestidge et al CA vol. 102, 1985 #77013p.

Mizel, et al., *Journal of Immunology*, vol. 131, No. 4, Oct. 1983, pp. 1834 to 1837.
Sofer, *Biotechnology*, Dec. 1984, pp. 1035–1038.
*The Peptides*, 1983, eds Greess et al, p. 39.
Sofer et al *Biotechniques*, Nov./Dec. 1983, pp. 198–203.
Sofer et al. *Biotechniques* Nov.–Dec., 1983, pp. 198–203.
Matsushima et al *Biochemistry* 25(12) 1986, pp. 3424–3429.
Bonneyen et al *Biotechnology* vol. 4, 1986, pp. 954–958.
Kronheim et al *J. Exp. Med* 161, 1985, p. 490.
Rimsky et al, *J Immunol* 136, 1986, p. 3384.
Biochemical Engineering 2nd ed Academic Press 1973 (346–92 pages vary).
Chem. Abst. No. 2193229 vol. 102, 1985, Krakauer.
Prestidge et al, *J Cell. Biochem.* 20, 1984, pp. 65–73.
Cerretti et al., European Patent Application Publication No. 165 654 A2.
Kronheim et al., Bio/Technology 4:1078 (1986).
Kung et al., European Patent Application No. 147 819 A2.
Taniguchi et al., European Patent Application Publication No. 118 617 A2.
Kung et al., Australian Patent Application Publication No. AU–A–36995/84.
Auron et al. PNAS, USA 81, 7970 (1984) "Cloning and Expression Recombinant Human IL–1β".
March et al. Nature 315, 641 (1985) "Cloning and Expression Recombiant Human IL–1α and IL–1β".
Oppenheim et al, *Immunol Today* 7(2) 1986, pp. 45–56.
Clark et al, *Nuc. Acid Res* 14(20) 1986, pp. 7897–7914.
Furutani et al, Nuc Acid Res 14(9) 1986, pp. 3167–3179.
Mizel et al *J Immunol* 126, 1981, pp. 834–837.
Windle et al *J. Immunol* 1984, vol. 132(3) pp. 1317–1322.
Cameron et al, *J Exp Med* 162, 1985, pp. 790–801.

*Primary Examiner*—Garnette D. Draper
*Attorney, Agent, or Firm*—George W. Johnston; William H. Epstein; Briana C. Buchholz

[57] ABSTRACT

A process for the production of essentially homogeneous soluble, stable, endotoxin free human recombinant interleukin-1α of enhanced specific activity is described. The process involves breaking transformed microbial cells containing expressed human interleukin-1α and separating the soluble supernatant from the insoluble cell components and then passing the supernatant through gel chromatography and ion-exchange chromatography steps.

7 Claims, 3 Drawing Sheets

PURIFICATION OF RECOMBINANT HUMAN IL-1α

BACKGROUND OF THE INVENTION

The cloning and expression of the gene for human interleukin-1α has been described in the art. See for example U.S. patent application Ser. No. 748,632 filed Jun. 24, 1985 entitled Recombinant Human Interleukin-1", inventors Gubler et al. The purification procedure described therein recognized that there was a problem due to the insolubility of this protein within the bacterial host cells. This insolubility problem is believed due to the production of high levels of protein in an environment which apparently is not conclusive to proper protein folding. The protein folding problems were manifested in the formation of inclusions within the bacteria. These inclusion bodies could be dissolved only in strong denaturing agents such as urea and guanidine hydrochloride.

The purification procedures utilizing these strong denaturing agents will achieve the desired goal of providing purified recombinant human IL-1α. However, for reasons not fully understood but believed to be related to the folding of the protein in this non-biolgical environment, the specific activity levels observed for the purified molecules did not exceed about $6\times10^6$ units/mg. Thus, a goal of the present invention was to develop a purification procedure for recombinant human interleukin-1, particularly recombinant human interleukin-1α, which would allow for purification and solubilization of the desired protein in a biologically compatible buffer system thus allowing the product to exhibit enhanced levels of specific activity.

The cloning of human interleukin-1β has been reported by Auron et al. Proc. Natl. Acad. Sci. USA 81 7970(1984) while March et al. have reported the cloning of both the α and β forms of human interleukin-1. See March et al., Nature 315 641 (1985).

SUMMARY OF THE INVENTION

The amino acid sequence of the human interleukin-1α of this invention is:

The present invention relates to an improved process for producing recombinant human interleukin-1, particularly human interleukin-1α as an essentially homogeneous protein, essentially endotoxin free and having an enhanced specific activity, specifically a specific activity of at least about $5\times10^7$ Units/mg. The amino acid sequence of the recombinant human interleukin-1α (IL-1α) is shown in FIG. 1. In addition, the invention relates to the novel form of recombinant human interleukin-1α produced by the instant process.

An important aspect of the present invention arises from the unexpected discovery that a substantial proportion of expressed recombinant human interleukin-1 in a bacterial host e.g. *E. coli*, is found in the soluble cytosol fraction even though the inchoate specific activity in this fraction is well below that contained in urea extracted inclusion bodies. Moreover not only is human interleukin-1α found in the cytosol but most surprisingly it has been further discovered that it can be purified from the cytosol in a simple two or optionally three step column chromatographic separation procedure.

In the first process step of the instant invention, the soluble cell fraction obtained by breaking the transformed microbial hosts which had been grown under conditions selected to cause expression of the introduced gene for human interleukin-1 and separated from the insoluble cell materials including the inclusion bodies where the prior art believed the great majority of the expressed human interleukin-1 was located.

The breaking of the cells can be accomplished by techniques well known in the art such as, for example, by use of enzymatic degradation e.g. with lysozyme treatment, by physical disruption using a ball mill or similar device or most preferably by sonication. Separation of the soluble cytosol from the insoluble cell materials is most conveniently carried out by centrifugation e.g. at 20,000×g for about 30 minutes. The cytosol fraction containing soluble recombinant human IL-1α is then subjected to size gel chromatography using a buffered salt solution for elution. A suitable column for this process step is a Sephacryl-200 column.

|     |     |     |     | Phe | Leu | Ser | Asn | Val | Lys | Tyr | Asn | Phe | Met | Arg | Ile |
| --- | --- | --- | --- | --- | --- | --- | --- | --- | --- | --- | --- | --- | --- | --- | --- |
| Ile | Lys | Tyr | Glu | Phe | Ile | Leu | Asn | Asp | Ala | Leu | Asn | Gln | Ser | Ile | Ile |
| Arg | Ala | Asn | Asp | Gln | Tyr | Leu | Thr | Ala | Ala | Ala | Leu | His | Asn | Leu | Asp |
| Glu | Ala | Val | Lys | Phe | Asp | Met | Gly | Ala | Tyr | Lys | Ser | Ser | Lys | Asp | Asp |
| Ala | Lys | Ile | Thr | Val | Ile | Leu | Arg | Ile | Ser | Lys | Thr | Gln | Leu | Tyr | Val |
| Thr | Ala | Gln | Asp | Glu | Asp | Gln | Pro | Val | Leu | Leu | Lys | Glu | Met | Pro | Glu |
| Ile | Pro | Lys | Thr | Ile | Thr | Gly | Ser | Glu | Thr | Asn | Leu | Leu | Phe | Phe | Trp |
| Glu | Thr | His | Gly | Thr | Lys | Asn | Tyr | Phe | Thr | Ser | Val | Ala | His | Pro | Asn |
| Leu | Phe | Ile | Ala | Thr | Lys | Gln | Asp | Tyr | Trp | Val | Cys | Leu | Ala | Gly | Gly |
| Pro | Pro | Ser | Ile | Thr | Asp | Phe | Gln | Ile | Leu | Glu | Asn | Gln | Ala. |     |     |

The size gel chromatography fractions contained in buffered salt solution, preferably Tris/HCl pH 8.0 buffered NaCl which may contain a protein stabilizer such as ethylenediaminetetraacetic acid (EDTA) are assayed. The combined active fractions are diluted with additional buffered salt solution and used in the second process of the invention.

Assay of the chromatographic fractions can be readily accomplished by methodologies well known in the art. A suitable assay is the murine thymocyte proliferation assay described by Mizel et al., J. Immunol. 120, 1497 (1978).

The second process step involves ion exchange chromatography preferably using a DEAE-cellulose column and eluting with a gradient of increasing concentration of buffered salt solution. In a preferred embodiment, a 0–800 mM NaCl gradient in Tris/HCl (25 mM) pH 8.1 buffer is used to elut the purified recombinant human interleukin-1.

In the large scale purification, after centrifugation to remove cell debris, the nucleic acids are removed by a streptomycin sufate precipitation. One tenth volume (of the supernatant) of 10% w/v strep sulfate solution is added. The pH is maintained at 6.2 to 6.4 with 1N acetic acid. The suspension is spun at 20,000×g for 30 min. The proteins in the resultant supernatant solution are concentrated by adding ammonium sulfate to 60% saturation. The suspension is spun at 20,000×g for 30 minutes and the resultant pellet dissolved in a minimum volume of 25 mM Tris HCl pH 8.0 containing 800 mM NaCl.

In some instances, particularly in scaled up runs, endotoxin levels at this point may be elevated above allowable levels. Thus, an optional third step can be introduced to remove the endotoxin. Procedures known in the art can be employed for this purpose although a preferred procedure in accordance with the instant invention involves the passage of the product solution (diluted 1:1 v/v with 25 mM Tris-HCl, pH 8.1) from the DEAE step through a column packed with Detoxi-Gel™ (Pierce Chemical Company, Rockford, Ill.) using the instructions provided by the manufacturer.

DESCRIPTION OF THE DRAWINGS

This invention may be more readily understood by reference to the following figures, in which FIG. 1 provides a chromatogram of the gel filtration of *E. coli* cytosol (soluble recombinant human interleukin-1α) on Sephacryl S-200. The eluent is 30 mM Tris/HCl pH 8.0 containing 800 mM NaCl. Aliquots of fractions were quantitated for IL-1 activity by the LAF assay.

DESCRIPTION OF PREFERRED EMBODIMENT

Figure 1:
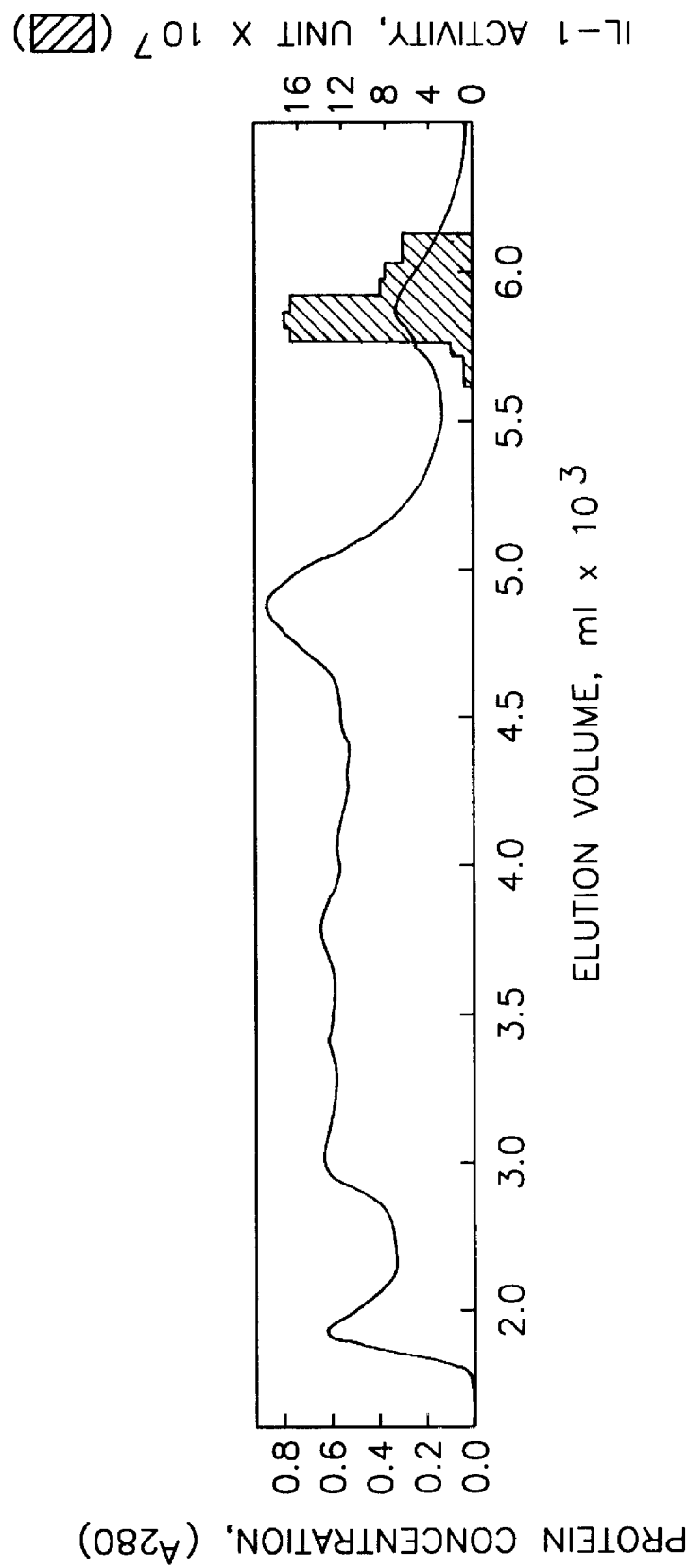
Figure 2:
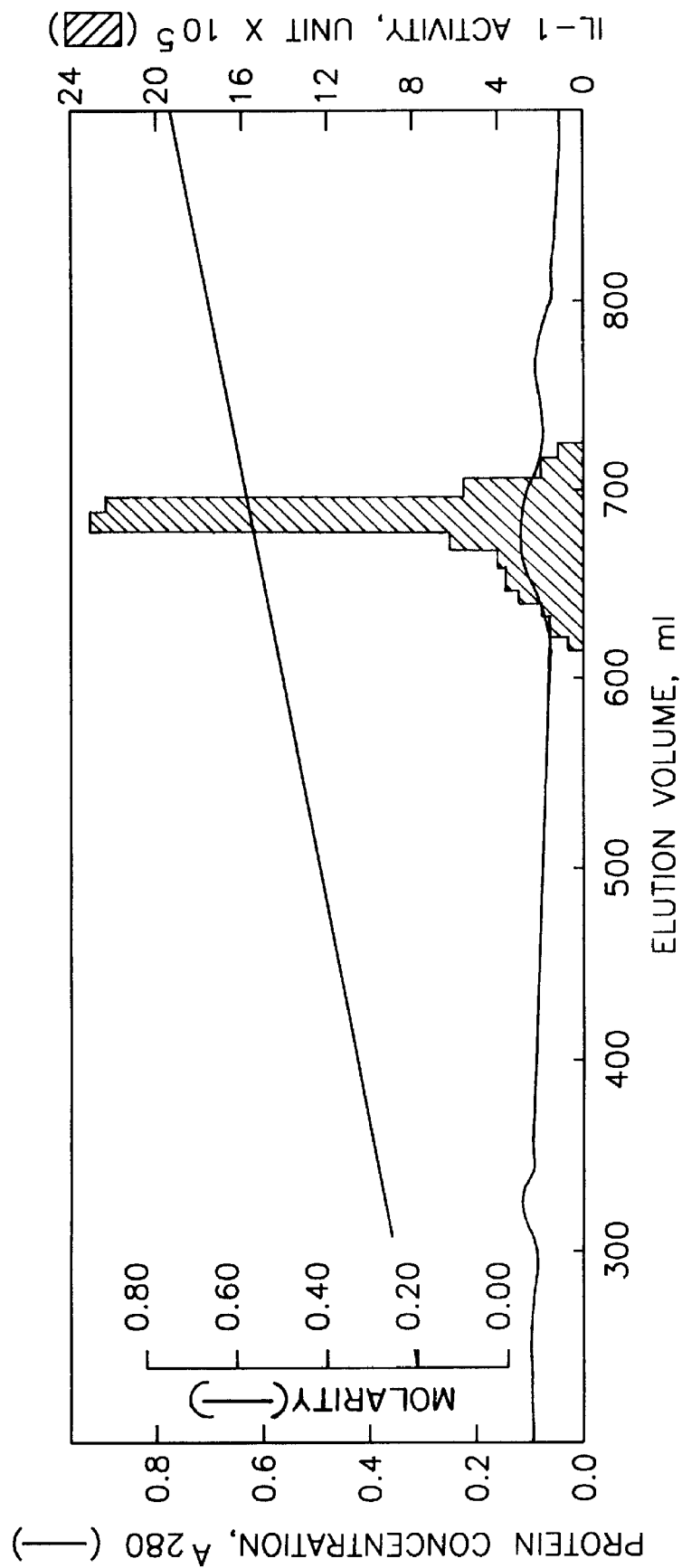
FIG. 2 shows a chromatogram of the DEAE-cellulose chromatography of S-200 pool of IL-1 active fractions. IL-1α was eluted with a salt gradient running from 0–800 mM NaCl/Tris HCl (25 mM), pH 8.1. Samples of each fraction were assessed for biological activity by the LAF assay.
Figure 3A:
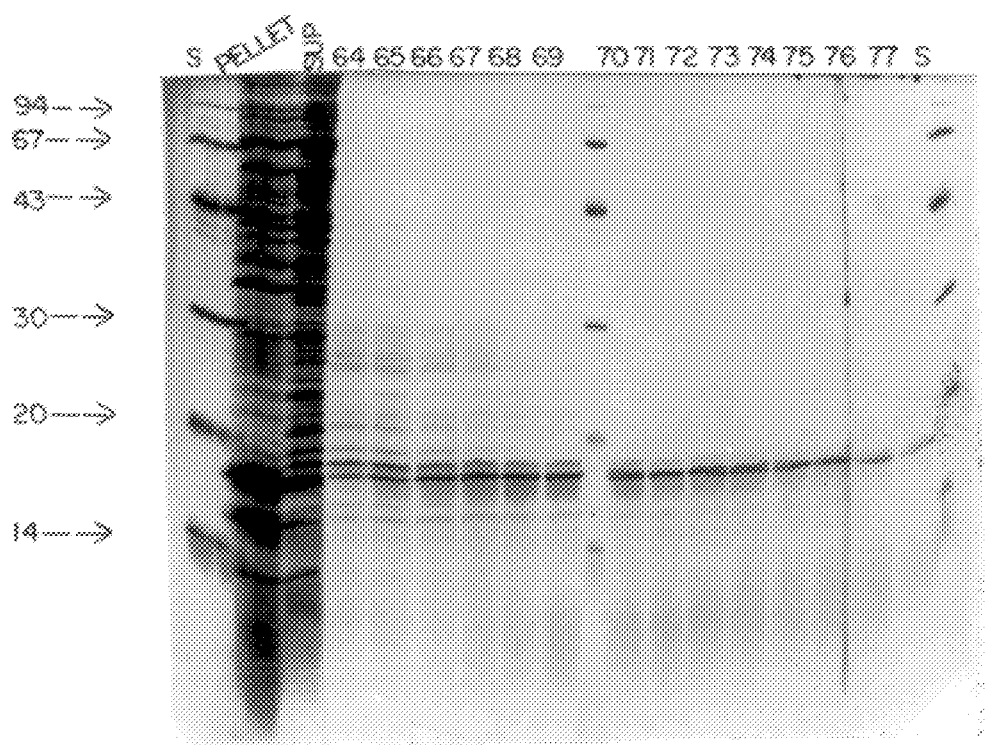
FIG. 3 demonstrates the purification of recombinant human interleukin-1α. Samples from stages in the purification of IL-1α were analyzed by SDS-PAGE. Lanes: (A) Pellet, pellet resulting from centrifugation of sonicated cell suspension; sup, cytosol fraction; 14993-1, 64–77, fractions 64 through 77 resulting from Sephacryl S-200 chromatography. (B) OR, pooled fractions from the S-200 column chromatography; dil OR, pooled fractions from the S-200 column chromatography diluted 1:3 v/v with 30 mM Tris HCl, pH 8.1; 14993-7, 60–73, fractions 60–73 resulting from the DEAE-cellulose chromatography. The electrophoretic mobilities of marker proteins (phosphorylase b, bovine serum albumin, ovalbumin, carbonic anhydrase, soybean trypsin inhibitor and α-lactalbumin) and their $M_r$ values ($\times 10^3$) are shown by arrows.
Figure 3B:
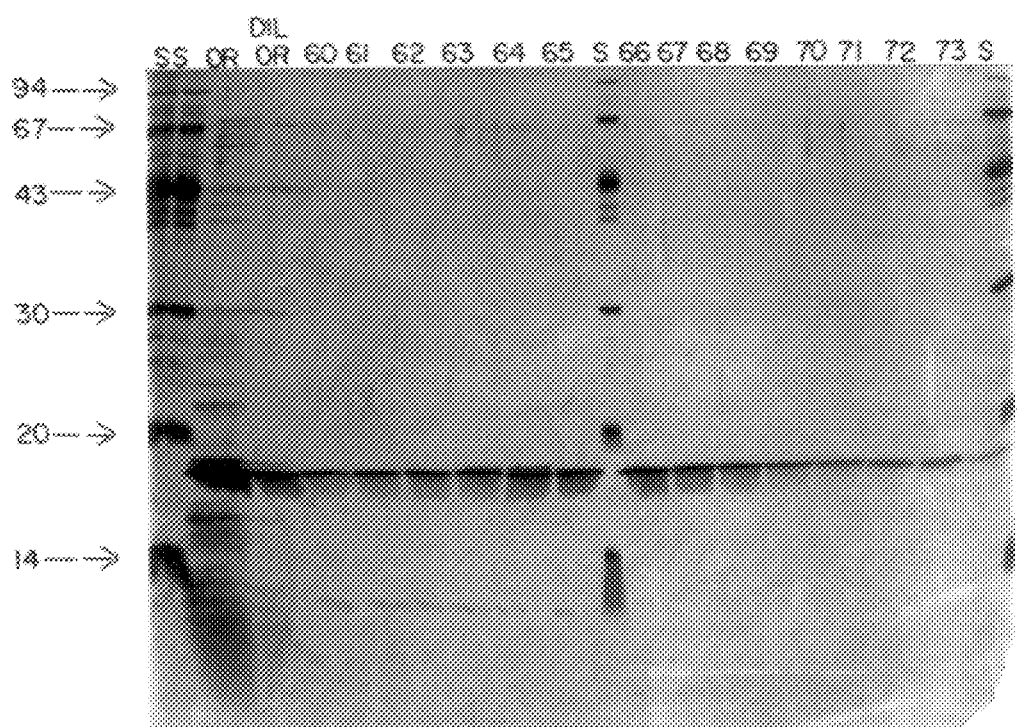

Frozen *E. coli* cells (containing the plasmid for human IL-1α as described-in U.S. Ser. No. 748,632 whose examples are incorporated herein by reference) were thawed in 30 mM Tris/HCl, pH 8.0, 5 mM EDTA (in a ratio of 1:5 w/v). The suspended cells were broken with a Branson Cell Disruptor 350 (sonicator). The broken cells and any "insoluble" human IL-1α in the form of inclusion bodies were removed by centrifugation at 20,000×g and the supernatant containing soluble recombinant human interleukin-1α was applied to a Sephacryl S-200 size exclusion column (FIG. 1). The column was equilibrated in 30 mM Tris/HCl, pH 8.0 containing 800 mM NaCl and 5 mM EDTA. The biologically active fractions were pooled, diluted 1:3 v/v with 30 mM Tris/HCl, pH 8.0 and chromatographed on DEAE-cellulose (Whatman Anion Exchanger DE 53) using a linear gradient of 0–800 mM NaCl in 25 mM Tris/HCl, pH 8.1 (FIG. 2). Greater than 50% of the biological activity was recovered with the protein containing a specific activity of 0.4 to $1.0 \times 10^7$ U/mg of protein. The purity of the protein was confirmed by SDS-PAGE analysis (FIG. 3) and reversed-phase HPLC. After S-200 chromatography, the recombinant human interleukin-1α was contaminated with 1000–2000 endotoxin units/ml but DEAE-chromatography resulted in a 99% reduction of endotoxin. The biological activity has been shown to be stable for at least three months when the protein is stored at 4° C.

This procedure was scaled up to produce 32 mg of essentially pure recombinant human interleukin-1α. One hundred (100) g of cell paste was processed through the Manton-Gaulin and the resultant soluble product was treated with streptomycin sulfate and ammonium sulfate as above to remove nucleic acids and concentrate protein and the resulting resolubilized protein in buffered salt solution chromatographed on a 10 liter S-200 column. The purified material was then chromatographed on a DEAE-cellulose column. The protein was greater than 95% pure as determined by SDS-PAGE. The total activity obtained was $1.6 \times 10^9$ U with an average specific activity of $5 \times 10^7$ U/mg. However, as opposed to the initial pilot run, this material was somewhat contaminated with endotoxin (up to 500 EU/ml). This endotoxin contaminant could be readily removed by passing the protein solution over a column packed with Detoxi-Gel™ (Pierce Chemical Company, Rockford, Ill.) following the instructions of the manufacturer.

I claim:

1. Recombinant human interleukin-1α as a homogeneous protein, essentially endotoxin free, having a specific activity of about $5 \times 10^7$ Units/mg measured by thymocyte proliferation assay.

2. Recombinant human interleukin 1α of claim 1 having the following amino acid sequence:

Phe  Leu  Ser  Asn  Val  Lys  Tyr  Asn  Phe  Met  Arg  Ile

Ile  Lys  Tyr  Glu  Phe  Ile  Leu  Asn  Asp  Ala  Leu  Asn  Gln  Ser  Ile  Ile

-continued

| | | | | | | | | | | | | | | | |
|---|---|---|---|---|---|---|---|---|---|---|---|---|---|---|---|
| Arg | Ala | Asn | Asp | Gln | Tyr | Leu | Thr | Ala | Ala | Ala | Leu | His | Asn | Leu | Asp |
| Glu | Ala | Val | Lys | Phe | Asp | Met | Gly | Ala | Tyr | Lys | Ser | Ser | Lys | Asp | Asp |
| Ala | Lys | Ile | Thr | Val | Ile | Leu | Arg | Ile | Ser | Lys | Thr | Gln | Leu | Tyr | Val |
| Thr | Ala | Gln | Asp | Glu | Asp | Gln | Pro | Val | Leu | Leu | Lys | Glu | Met | Pro | Glu |
| Ile | Pro | Lys | Thr | Ile | Thr | Gly | Ser | Glu | Thr | Asn | Leu | Leu | Phe | Phe | Trp |
| Glu | Thr | His | Gly | Thr | Lys | Asn | Tyr | Phe | Thr | Ser | Val | Ala | His | Pro | Asn |
| Leu | Phe | Ile | Ala | Thr | Lys | Gln | Asp | Tyr | Trp | Val | Cys | Leu | Ala | Gly | Gly |
| Pro | Pro | Ser | Ile | Thr | Asp | Phe | Gln | Ile | Leu | Glu | Asn | Gln | Ala | | | with an N-terminus methionine group.

3. A process for producing human interleukin-1α as an essentially homogeneous protein, essentially endotoxin free and having a specific activity of at least about $5 \times 10^7$ Units/mg which process comprises breaking microbial cells which had been transformed with an expression vector containing the gene for human interleukin-1α and expression of said gene induced, separating insoluble cell materials from a supernatant fraction, passing said supernatant over a gel size exclusion chromatographic column and eluting with a buffered salt solution, combining the active fractions from said gel column and passing said active fractions over an ion-exchange chromatography column eluting said desired protein with a gradient of buffered salt solution of increasing concentration.

4. The process of claim 3 wherein endotoxin present in gel filtration chromatography eluent is removed by ion-exchange chromatography.

5. The process of claim 3 wherein said microbial cells are broken by sonication.

6. The process of claim 3 wherein said gel size exclusion chromatographic column is a Sephacryl S-200 column and said buffered salt solution is Tris buffered NaCl.

7. The process of claim 3 wherein said ion-exchange column is a DEAE-cellulose column and said buffered salt solution gradient is a Tris buffered 0–800 mM NaCl solution gradient.

* * * * *